(12) United States Patent
Mattar

(10) Patent No.: US 6,997,032 B2
(45) Date of Patent: Feb. 14, 2006

(54) FLOWMETER ZEROING TECHNIQUES

(75) Inventor: Wade M. Mattar, Wrentham, MA (US)

(73) Assignee: Invensys Systems, Inc., Foxboro, MA (US)

( * ) Notice: Subject to any disclaimer, the term of this patent is extended or adjusted under 35 U.S.C. 154(b) by 0 days.

(21) Appl. No.: 10/729,990

(22) Filed: Dec. 9, 2003

(65) Prior Publication Data

US 2004/0200259 A1    Oct. 14, 2004

Related U.S. Application Data

(60) Provisional application No. 60/460,817, filed on Apr. 8, 2003.

(51) Int. Cl.
*G01F 1/84* (2006.01)

(52) U.S. Cl. .......................................... 73/1.34; 73/1.16

(58) Field of Classification Search ........ 73/1.16–1.36; 702/87, 88, 100
See application file for complete search history.

(56) References Cited

U.S. PATENT DOCUMENTS

| | | | |
|---|---|---|---|
| 4,817,448 A | | 4/1989 | Hargarten et al. |
| 4,852,409 A | | 8/1989 | Herzl |
| 5,228,327 A | | 7/1993 | Bruck |
| 5,524,084 A | * | 6/1996 | Wang et al. ................. 702/100 |
| 5,796,012 A | | 8/1998 | Gomi et al. |
| 6,272,438 B1 | * | 8/2001 | Cunningham et al. ......... 702/56 |
| 6,311,136 B1 | | 10/2001 | Henry et al. |
| 6,367,336 B1 | * | 4/2002 | Martina et al. ........... 73/861.74 |
| 6,374,190 B2 | * | 4/2002 | Schupfner ..................... 702/94 |
| 6,378,354 B1 | * | 4/2002 | Sharp ......................... 73/1.16 |
| 6,505,519 B2 | | 1/2003 | Henry et al. |
| 6,687,635 B2 | * | 2/2004 | Horne et al. .................. 702/86 |

OTHER PUBLICATIONS

Endress & Hauser, "promass 63—Mass Flow Measuring System"; BA 014D/06/en/08.97, 7 pages.

* cited by examiner

*Primary Examiner*—Robert Raevis
(74) *Attorney, Agent, or Firm*—Fish & Richardson, P.C.

(57) ABSTRACT

Descriptions are provided for implementing flowmeter zeroing techniques. In operating a flowmeter, it may be the case that, if not properly calibrated, the flowmeter will produce erroneous measurements, e.g., will indicate a non-zero flow during a period of zero flow. By determining a magnitude of such erroneous measurements, calibration values may be determined, which may later be used to adjust a measurement that is output by the flowmeter and thereby improve an accuracy of the flowmeter. Such calibration values may be determined for a plurality of operational conditions associated with the flowmeter, such as densities of materials being measured, and/or configurations of flow elements associated with transporting material to the flowmeter. Then, the calibration values may be correlated with the relevant operational conditions, and stored for later use. In this way, during an actual operation of the flowmeter, a number of calibration values may be made available, and an optimal calibration value may be selected for an existing operational condition of the flowmeter.

33 Claims, 6 Drawing Sheets

FLOWMETER ZEROING TECHNIQUES

CROSS-REFERENCE TO RELATED APPLICATIONS

This application claims priority to U.S. Provisional Application Ser. No. 60/460,817, filed on Apr. 8, 2003, and titled "FLOWMETER ZEROING TECHNIQUES," which is incorporated by reference.

TECHNICAL FIELD

This description relates to flowmeters.

BACKGROUND

Flowmeters provide information about materials being transferred through a conduit. For example, mass flowmeters provide a measurement of the mass of material being transferred through a conduit. Similarly, density flowmeters, or densitometers, provide a measurement of the density of material flowing through a conduit. Mass flowmeters also may provide a measurement of the density of the material.

For example, Coriolis-type mass flowmeters are based on the Coriolis effect, in which material flowing through a conduit becomes a radially-travelling mass that is affected by a Coriolis force and therefore experiences an acceleration. Many Coriolis-type mass flowmeters induce a Coriolis force by sinusoidally oscillating a conduit about a pivot axis orthogonal to the length of the conduit. In such mass flowmeters, the Coriolis reaction force experienced by the traveling fluid mass is transferred to the conduit itself and is manifested as a deflection or offset of the conduit in the direction of the Coriolis force vector in the plane of rotation.

SUMMARY

According to one general aspect, a flowmeter is calibrated. A plurality of calibration values are determined, the calibration values corresponding to measurements of material in a flowtube, the flowtube being associated with the flowmeter. Each of the calibration values is associated with one of a plurality of operational parameters of the flowmeter, each of the operational parameters being present during the determining of its corresponding calibration value. The calibration values are stored in association with their respective operational parameters.

Implementations may have one or more of the following features. For example, in determining the plurality of calibration values a plurality of zero-flow calibration values corresponding to the measurements may be determined, where the measurements include mass flow measurements erroneously indicated by the flowmeter during a time of substantially zero mass flow through the flowtube. A current operational parameter of the flowmeter may be determined, and a current calibration value for use during an obtaining of a mass flow measurement may be determined, based on the current operational parameter.

In determining the current operational parameter, a density of the material in the flowtube may be determined. In this case, determining the current calibration value of the flowmeter may include measuring a current density of a current material in the flowtube.

In associating each of the calibration values with one of the plurality of operational parameters, a first calibration value may be associated with a range of densities. In this case, in determining the current calibration value, a current density of a current material in the flowtube may be measured, it may be determined that the current density falls within the range of densities, and the first calibration value may be selected.

In associating each of the calibration values with one of the plurality of operational parameters, a mathematical relationship between the calibration values and the plurality of operational parameters may be used. In this case, in determining the current calibration value, a current density of a current material in the flowtube may be measured, the current density may be used in conjunction with the mathematical relationship to determine a current calibration value, and the current calibration value may be selected.

In determining the current operational parameter, a configuration of flow elements associated with the flowtube may be determined. In this case, in determining the current calibration value, an input may be accepted from a user, the input identifying a current configuration of flow elements. Additionally, or alternatively, in determining the current calibration value, a first density of a first material in the flowtube may be measured, a correlation between the first density and a first configuration of flow elements may be accessed, and a first calibration value corresponding to the first configuration may be selected.

In determining the current operational parameter, a gas void fraction of the material in the flowtube may be determined. In this case, in determining the current calibration value, an input of the gas void fraction may be received from a gas void fraction measurement system, and the current calibration value may be selected from a pre-determined list of associated calibration values and gas void fractions.

According to another general aspect, a calibration system includes a measurement system operable to output measurements of material in a flowtube, where the flowtube is associated with a flowmeter, a calibration system operable to determine calibration values, each based on a corresponding measurement output by the measurement system, and a memory operable to store each of the calibration values in conjunction with an operational parameter associated with an operation of the flowmeter at a time of the corresponding measurement.

Implementations may have one or more of the following features. For example, the calibration system may be operable to select a calibration value from the memory, based on a current operational parameter associated with the flowmeter. The measurement may include a mass flow rate of the material, and further wherein the calibration values may include zero calibration values corresponding to erroneously-detected mass flow measurements of the material during a time of substantially zero flow.

The operational parameter may include a density of the material. The calibration system may be operable to select a current calibration value based on a current density of material in the flowtube, as measured by the measurement system. The calibration system may be operable to select the current calibration value by associating the current density with a pre-selected range of densities that is stored in the memory in association with the current calibration value. The calibration system may be operable to select the current calibration value, based on the current density and a mathematical relationship between the calibration values and their corresponding operational parameters The operational parameter may include a configuration of flow elements associated with the flowtube. The calibration system may be operable to accept a current configuration input by an operator, and to select a current calibration value based on the current configuration. The calibration system may be operable to select a current calibration value by determining a current configuration based on a currently-measured density that was previously associated with the current configuration.

The operational parameter may include a gas void fraction of flow elements within the flowtube. The calibration system may be operable to receive a current gas void fraction from a gas void fraction measurement system, and further may be operable to select a corresponding current calibration value from the memory.

The measurement system, the calibration system, and the memory may be integrated with the flowmeter.

According to another general aspect, a flowmeter is operated. An operational parameter associated with the flowmeter is determined. A zero-flow calibration value based on the operational parameter is determined, based on a plurality of previously-determined zero-flow calibration values. A measurement of a property of a material within a flowtube associated with the flowmeter is taken, using the flowmeter. The measurement is adjusted using the zero-flow calibration value.

Implementations may have one or more of the following features. For example, in determining the operational parameter, determining a configuration of flow elements associated with the flowtube may be determined. In determining the zero-flow calibration value, the zero-flow calibration value may be selected from among the previously-determined zero-flow calibration values as being the zero-flow calibration value that corresponds to one of a set of configurations, where each of the set of configurations existed at a time when its corresponding zero-flow calibration value was previously determined.

In determining the operational parameter, a selection of the configuration may be accepted from a pre-determined set of configurations. Additionally, or alternatively, a density of the material may be measured, and the density may be associated with a first configuration.

The operational parameter may include a density of the material in the flowtube. In this case, determining the zero-flow calibration value may include associating the density with a range of densities, and selecting the zero-flow calibration value from among the plurality of previously-determined zero-flow calibration values, based on a pre-determined relationship between the range of densities and the zero-flow calibration value.

In determining the zero-flow calibration value, the density may be input into a mathematical relationship derived from a relationship between the previously-determined zero-flow calibration values and corresponding density measurements. Additionally, or alternatively, the zero-flow calibration value may be selected from among the plurality of previously-determined zero-flow calibration values, based on a pre-determined relationship between the operational parameter and the zero-flow calibration value.

In determining the operational parameter, a gas void fraction of the material in the flowtube may be determined. In determining the gas void fraction, a current gas void fraction may be received from a gas void fraction measurement system, and further wherein determining the zero-flow calibration value comprises selecting a current zero-flow calibration value previously associated with the current gas void fraction measurement.

The details of one or more implementations are set forth in the accompanying drawings and the description below. Other features will be apparent from the description and drawings, and from the claims.

DETAILED DESCRIPTION

Types of flowmeters include digital flowmeters. For example, U.S. Pat. No. 6,311,136, which is hereby incorporated by reference, discloses the use of a digital flowmeter and related technology including signal processing and measurement techniques. Such digital flowmeters may be very precise in their measurements, with little or negligible noise, and may be capable of enabling a wide range of positive and negative gains at the driver circuitry for driving the conduit. Such digital flowmeters are thus advantageous in a variety of settings. For example, commonly-assigned U.S. Pat. No. 6,505,519, which is incorporated by reference, discloses the use of a wide gain range, and/or the use of negative gain, to prevent stalling and to more accurately exercise control of the flowtube, even during difficult conditions such as two-phase flow.

Although digital flowmeters are specifically discussed below with respect to FIGS. 1 and 2, it should be understood that analog flowmeters also exist. Although such analog flowmeters may be prone to typical shortcomings of analog circuitry, e.g., low precision and high noise measurements relative to digital flowmeters, they also may be compatible with the various techniques and implementations discussed herein. Thus, in the following discussion, the term "flowmeter" or "meter" is used to refer to any type of device and/or system in which a Coriolis flowmeter system uses various control systems and related elements to measure a mass flow, density, and/or other parameters of a material(s) moving through a flowtube or other conduit.

Figure 1A:
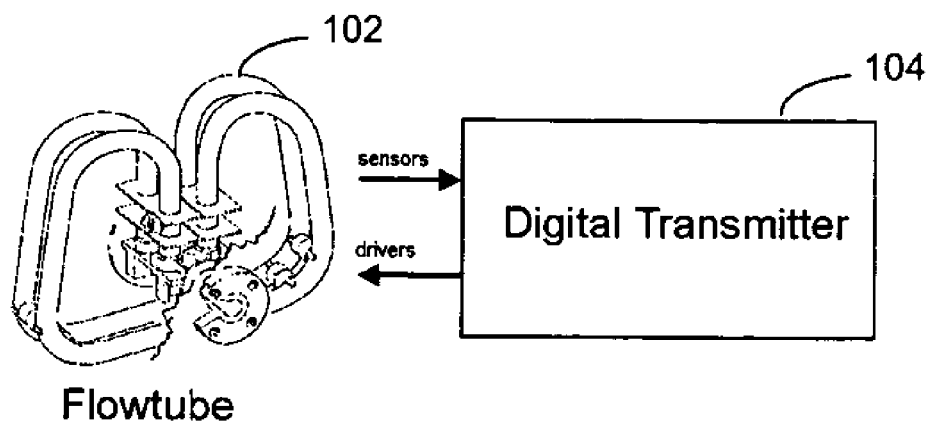
FIG. 1A is an illustration of a Coriolis flowmeter using a bent flowtube.

FIG. 1A is an illustration of a digital flowmeter using a bent flowtube 102. Specifically, the bent flowtube 102 may be used to measure one or more physical characteristics of, for example, a (traveling) fluid, as referred to above. In FIG. 1A, a digital transmitter 104 exchanges sensor and drive signals with the bent flowtube 102, so as to both sense an oscillation of the bent flowtube 102, and to drive the oscillation of the bent flowtube 102 accordingly. By quickly and accurately determining the sensor and drive signals, the digital transmitter 104, as referred to above, provides for fast and accurate operation of the bent flowtube 102. Examples of the digital transmitter 104 being used with a bent flowtube are provided in, for example, commonly-assigned U.S. Pat. No. 6,311,136.

Figure 1B:
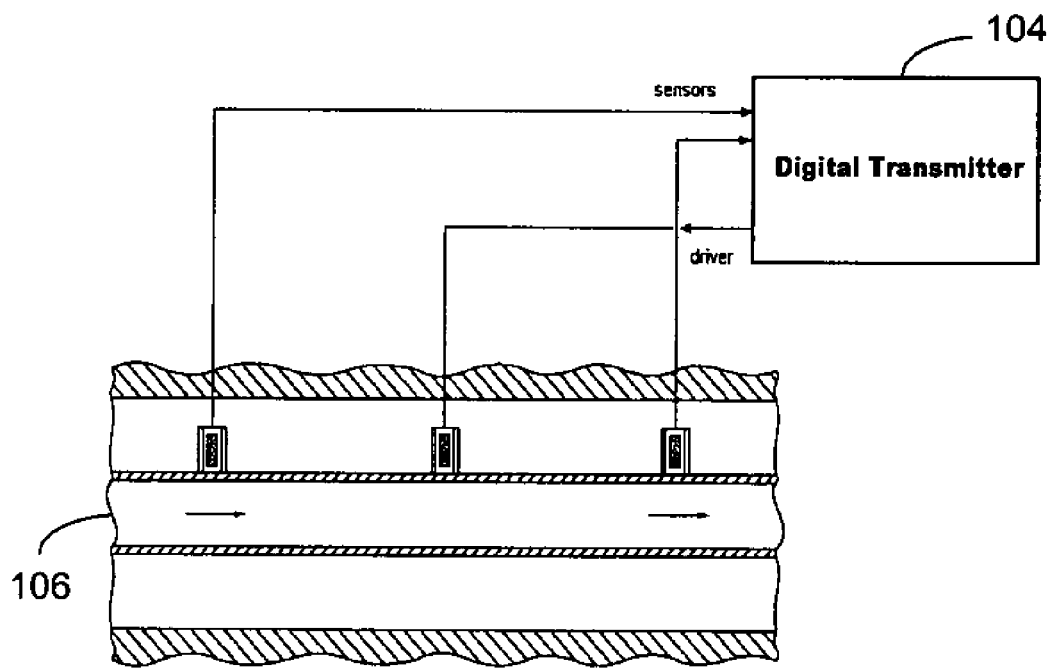
FIG. 1B is an illustration of a Coriolis flowmeter using a straight flowtube.

FIG. 1B is an illustration of a digital flowmeter using a straight flowtube 106. More specifically, in FIG. 1B, the straight flowtube 106 interacts with the digital transmitter 104. Such a straight flowtube operates similarly to the bent flowtube 102 on a conceptual level, and has various advantages/disadvantages relative to the bent flowtube 102. For example, the straight flowtube 106 may be easier to (completely) fill and empty than the bent flowtube 102, simply due to the geometry of its construction. In operation, the bent flowtube 102 may operate at a frequency of, for example, 50–110 Hz, while the straight flowtube 106 may operate at a frequency of, for example, 300–1,000 Hz.

Figure 2:
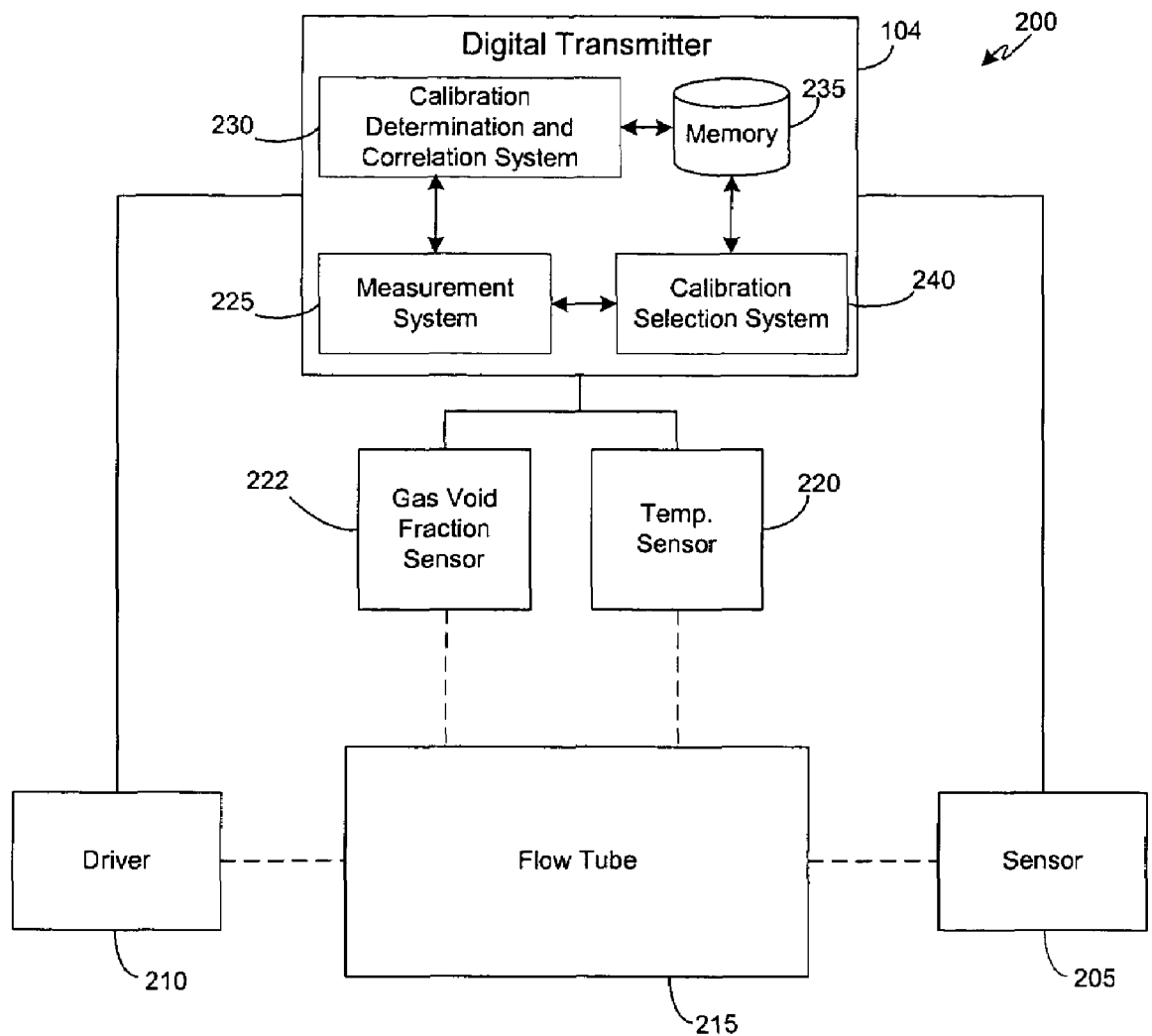
FIG. 2 is a block diagram of a Coriolis flowmeter.

Referring to FIG. 2, a digital mass flowmeter 200 includes the digital transmitter 104, one or more motion sensors 205, one or more drivers 210, a flowtube 215 (which also may be referred to as a conduit, and which may represent either the bent flowtube 102, the straight flowtube 106, or some other type of flowtube), and a temperature sensor 220. The digital transmitter 104 may be implemented using one or more of, for example, a processor, a Digital Signal Processor (DSP), a field-programmable gate array (FPGA), an ASIC, other programmable logic or gate arrays, or programmable logic with a processor core.

The digital transmitter 104 generates a measurement of, for example, density and/or mass flow of a material flowing through the flowtube 215, based at least on signals received from the motion sensors 205. The digital transmitter 104 also controls the drivers 210 to induce motion in the flowtube 215. This motion is sensed by the motion sensors 205.

Density measurements of the material flowing through the flowtube are related to, for example, the frequency of the motion of the flowtube 215 that is induced in the flowtube 215 by a driving force supplied by the drivers 210, and/or to the temperature of the flowtube 215. Similarly, mass flow through the flowtube 215 is related to the phase and frequency of the motion of the flowtube 215, as well as to the temperature of the flowtube 215.

The temperature in the flowtube 215, which is measured using the temperature sensor 220, affects certain properties of the flowtube, such as its stiffness and dimensions. The digital transmitter 104 may compensate for these temperature effects. This temperature affects, for example, an operating frequency of the digital transmitter 104, a sampling rate of an analog-to-digital converter, and/or a crystal frequency associated with a reference clock used by the transmitter 104. Also in FIG. 2, a gas void fraction sensor 222 (discussed in more detail below) is included that is operable to determine what percentage of a material in the flowtube 215, if any, is composed of a gas. Although not shown in FIG. 2, other sensors may be included, such as, for example, a pressure sensor that is operable to sense a pressure of a material flowing through the flowtube 215.

In performing measurements of mass flow (and/or density), calibration of the flowmeter may be required in order to maintain system performance, particularly over long periods of time and/or extensive operation of the flowmeter. One calibration technique is known as "zeroing" or "a zero calibration." In a zeroing process, a flow of material through the flowtube 215 is stopped (for example, upstream and downstream valves may be closed) during a time when the flowtube 215 is filled with the material. As a result, there is a zero flow of the material, which should lead to a corresponding reading of zero flow output by the flowmeter.

For various reasons, however, it may be the case that the flowmeter outputs a non-zero (i.e., erroneous) flowrate during a time of zero flow. In these cases, the (erroneous) non-zero flowrate at zero flow may be used as a calibration factor; that is, for example, it may be subtracted from (or added to) a measured flow, so as to obtain an accurate, i.e., zero-corrected, reading of the flow during future readings.

The zeroing process might involve, for example, filling the flowtube 215 with a process fluid. Then the flow is brought to zero while keeping the meter full. The resulting non-zero, erroneous flow indicated by the flowmeter may be averaged over a period of time to determine the zero calibration value.

In performing such a zeroing process, a type of flowtube currently being used may be relevant in obtaining and using the zero calibration value. Additionally, it may be the case that the zero calibration value also is a function of factors or parameters that are related to the particular operation of whatever flowmeter being used. That is to say, the zero calibration value may be a function of various parameters, such as, for example, a density of the process fluid(s), a configuration of external elements associated with the flowmeter (e.g., valves, pumps, pipes), or a temperature (as measured by the temperature sensor 220). As a result, when one or more of these parameters changes, the previously-calculated zero calibration value may be less accurate.

For example, in a Coriolis mass flowmeter, the zero calibration value may be different for fluids having different densities. One reason for this may be that the drive frequency for the flowtube 215 is selected in part based on fluid density, and the mass flow reading at zero flow may be largely dependent on frequency. Thus, in applications where fluids of greatly varying density are involved, or applications where multiple fluids are passed through the same meter, the calculated zero calibration value may not be sufficiently accurate.

As another example, the phrase "batching from empty" refers to a condition in which a flowmeter is completely emptied in between batches of measured materials (i.e., is empty at a start and finish of the measurements). In this situation, the zero calibration value when the flowtube 215 is full may be considerably different than the zero calibration value when the flowtube is empty. Other examples in which a zero calibration value may require changing in response to changed (or changing) flowmeter conditions are discussed in more detail below.

In order to provide an accurate zero calibration value in a wide variety of settings, separate zero calibration values are determined in different environments, and correlated with the environment in which they were obtained. Then, during subsequent use of the flowmeter, an appropriate zero calibration value is determined for the environment at hand, based on the previously-obtained values.

In FIG. 2, then, the digital transmitter 104 includes various elements designed to implement the above-described calibration functionality. It should be understood that some or all of these elements (along with other elements of the digital transmitter 104, not explicitly shown in FIG. 2) also may be used during a normal operation of the flowmeter 200 (e.g., after zero calibration values have been determined).

Thus, the digital transmitter 104 includes a measurement system 225, which is operable to obtain a measurement, such as a mass flow measurement and/or density measurement. A calibration determination and correlation system 230, based on at least one measurement output by the measurement system 225, determines a zero calibration value corresponding to an operational parameter of the flowmeter 200, at the time of the measurement. For example, the measurement system 225 may output an erroneous, non-zero measurement of mass flow of a given material during a time of substantially zero flow of the material through the flowtube 215, as well as a density of the material. The calibration determination and correlation system 230 may then determine a zero calibration value associated with the mass flow measurement and correlate that zero calibration value with the measured density, to be used as a correction factor during future mass flow measurements of material(s) having that density.

Thus, as in the example just given, the operational parameter may include, for example, a parameter that is detectable and measurable by the measurement system 225, such as the density (or temperature) of the material. As another example, the operational parameter may include a parameter that may be input into the calibration determination and correlation system 230 by an operator, such as a configuration of the flowmeter, or a configuration of various flow elements associated with the flowmeter, such as pipes, valves, or manifolds.

The calibration determination and correlation system 230 correlates particular zero calibration values with particular, corresponding operational parameters, and stores these values and correlations in a memory 235. During a subsequent operation of the flowmeter 200, a calibration selection system 240 may select or otherwise determine an appropriate zero calibration value, using the memory 235. In one implementation, the calibration system determines the appropriate zero calibration value automatically, whereas, in another implementation, an operator selects the appropriate zero calibration value directly from the memory 235. Thus, an appropriate zero calibration value is made available to the measurement system 225, so that the measurement system 225, during normal operation of the flowmeter 200, may output highly-accurate, zero-adjusted measurements.

The calibration selection system 240 may select a zero calibration value from the memory 235 in a variety of ways. For example, when zero calibration values and operational parameters that include a corresponding number of fluid densities are stored in the memory 235, the calibration selection system 240 may interact with the measurement system 225 to determine a density of a material currently in the flowtube 215. Then, the calibration selection system may select a zero calibration value corresponding to that density. In this way, highly-accurate, customized mass flow measurements may be obtained during future use of the flowmeter, even when a plurality of different-density materials are measured by the flowmeter.

Figure 3:
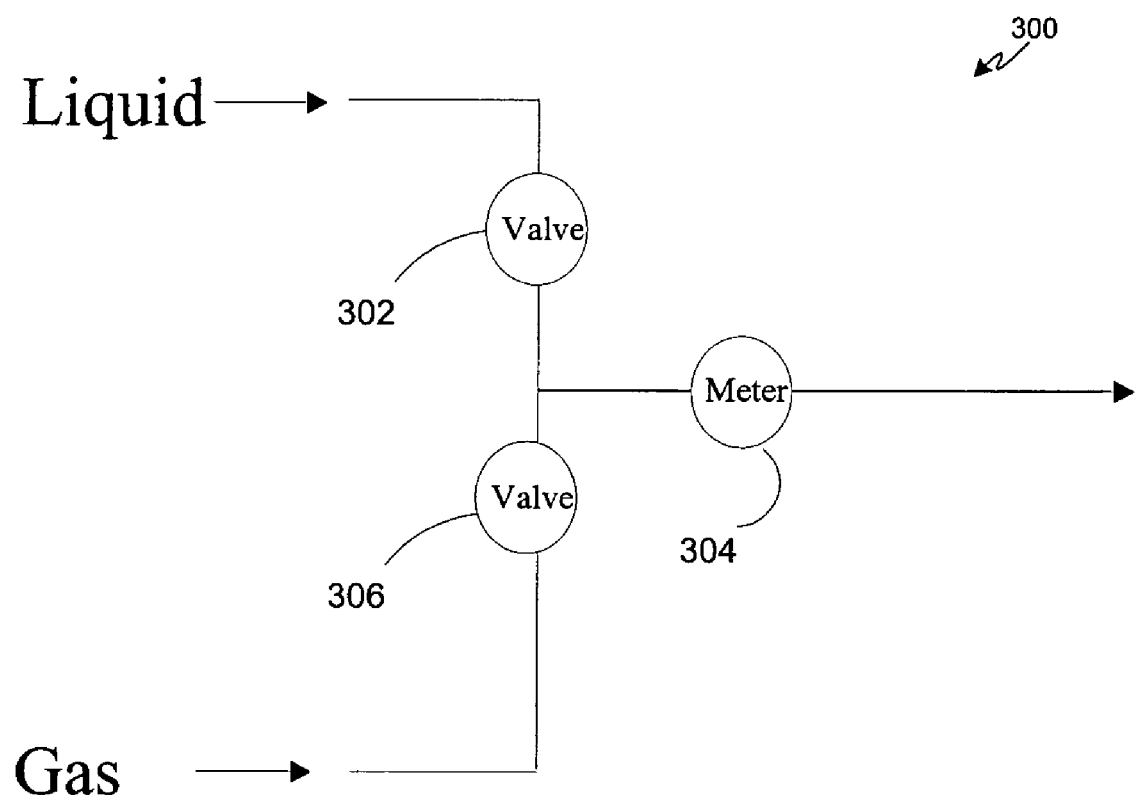
FIG. 3 is a block diagram of a flowmeter operating in conjunction with one or more of a plurality of different-density materials.

FIG. 3 is a block diagram 300 of a flowmeter operating in conjunction with one or more of a plurality of different-density materials. In FIG. 3, a liquid material is fed into a valve 302, and thereby into a meter 304. Further in FIG. 3, a vapor or gas material is fed through a valve 306 and into the meter 304. It should be understood that, although not explicitly shown in FIG. 3, the meter 304 may include, for example, all of the features described above with respect to the flowmeter 200 and further described in U.S. Pat. Nos. 6,311,136 and/or 6,505,519.

In FIG. 3, the valve 302 may be opened while the valve 306 is closed, so that the meter 304 measures only the liquid material. Conversely, the valve 306 may be opened while the valve 302 is closed, so that the meter 304 measures only the gaseous material. Further, the valves 302 and 306 may each be partially or alternately open, so that both of the liquid and gaseous materials travel through the meter 304 during a given period of time.

Thus, as described above, a density of the liquid and a density of the gas (e.g., air) may be associated with an appropriate zero calibration value. Then, during subsequent measurements, the meter 304 may determine a density of the material currently flowing therethrough, and select the corresponding zero calibration value accordingly.

It should be understood that many variations exist for the configuration shown in FIG. 3. For example, more than two materials could be measured in this way by the meter 304. Also, multiple types of liquids (or gasses) could simultaneously be included (as opposed to one or more of each).

In one implementation, a mixture of the same two fluids is passed through the meter 304, where proportions of the fluids relative to one another may vary. For example, in FIG. 3, the liquid and the gas may be passed through the meter 304 simultaneously, rather than consecutively, and the percentage of the gas (i.e., the "void fraction") may vary over time. As the void fraction increases, the density of the liquid/gas mixture will generally decrease, possibly resulting in the need for a different zero calibration value.

Various techniques exist for measuring the gas void fraction. For example, various sensors or probes exist that may be inserted into the flow to determine a gas void fraction.

As another example, a venturi tube (i.e., a tube with a constricted throat that determines fluid pressures and velocities by measurement of differential pressures generated at the throat as a fluid traverses the tube), relying on the fact that gas generally moves with a higher velocity than liquid(s) through a restriction, may be used to determine a pressure gradient and thereby allow a determination of the gas void fraction. In some systems, as referred to above with respect to FIG. 2, measurements of gas void fractions may be obtained using equipment (e.g., the gas void fraction sensor 222) that is wholly external to the flowtube. For example, sonar measurements may be taken to determine gas void fraction. As a specific example of such a sonar-based system, the SONARtrac™ gas void fraction monitoring system produced by CiDRA Corporation of Wallingford, Conn. may be used.

The situation of a void fraction arises, for example, when the meter 304 measures a liquid and gas flow simultaneously (e.g., when measuring a combination of oil and hydrocarbon-related gas that is output by an oil well), or when a meter is used in a "batching from empty" application, as referred to above. In these and similar situations, the user might, for example, zero the meter 304 while full of liquid, and store the zero calibration value and density. This process may be repeated with the meter 304 being empty (e.g. full of air). Then, during operation, the meter 304 would use the zero calibration value associated with gas when it is predominantly gas and would use the zero calibration value associated with liquid when it is closer to being full. This process could be further extended to store zero calibration values for a variety of void fractions.

Additionally, or alternatively, any of the various techniques discussed above for determining gas void fractions (or any other technique) may be used to determine gas void fractions, which may then be associated with corresponding zero calibration values. In one implementation, a gas void fraction measurement system, such as, for example, an external sensor or probe similar to those discussed above, may output a signal directly to an input of the transmitter 104, to be processed in the transmitter 104 to determine a gas void fraction (i.e., may be positioned and connected similarly to the temperature sensor 220 of FIG. 2). In another implementation, the signal from such an external sensor or probe may be connected to a separate computing resource, such as, for example, a control system or flow computer, with the determination of a gas void fraction carried out therein. In yet another implementation, the sensor or probe itself may have an integrally-formed computing resource that is operable to determine a gas void fraction for direct output to the transmitter 104.

Figure 4:
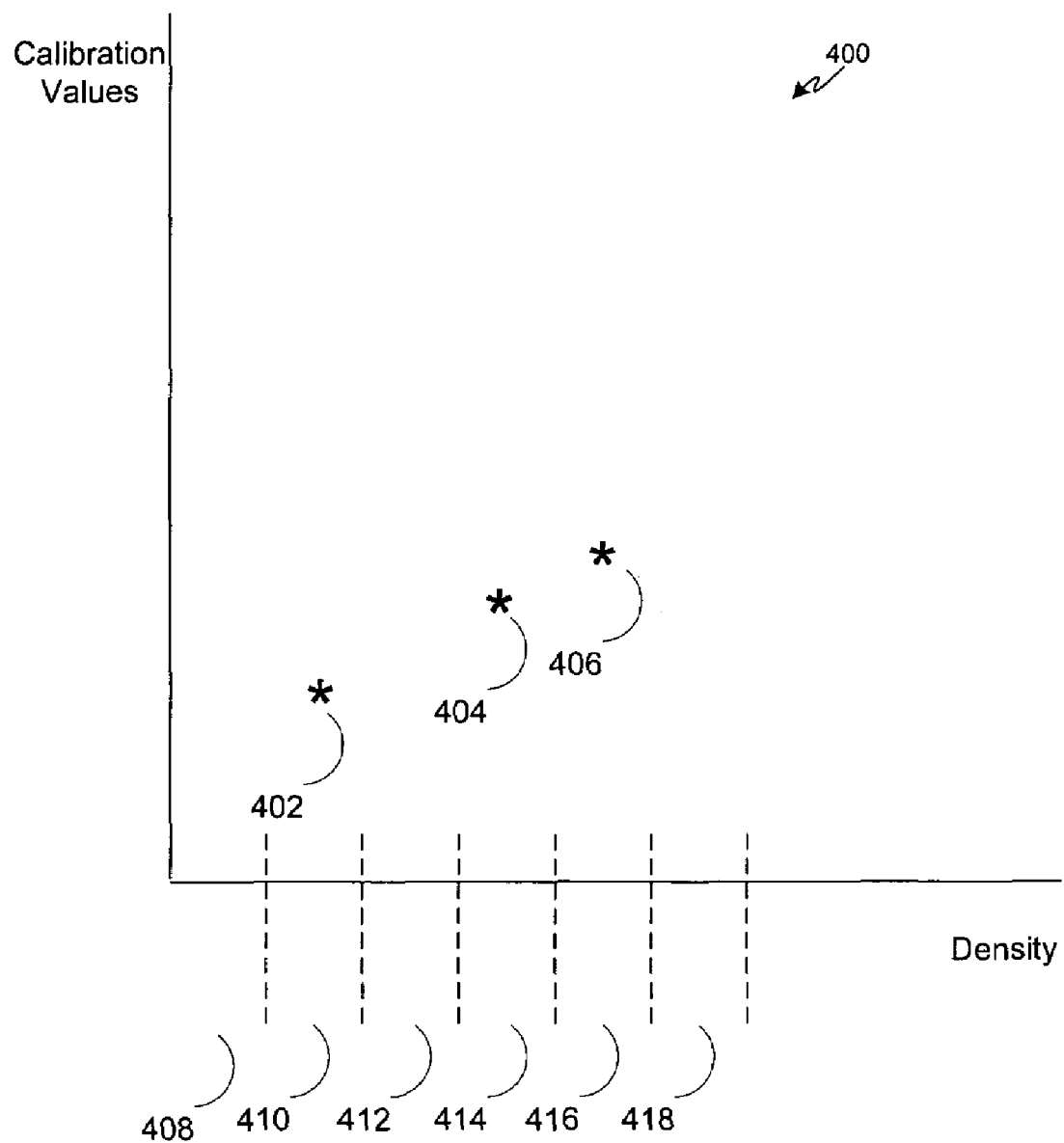
FIG. 4 is a chart comparing zero calibration values calculated at different fluid densities.

FIG. 4 is a chart 400 comparing zero calibration values calculated at different fluid densities. In the chart of FIG. 4, a first data point 402 corresponds to a zero calibration value determined (by the calibration determination and correlation system 230) for a material having a first density, as measured by the measurement system 225. Similarly, second and third data points 404 and 406 correspond to zero calibration values determined for materials having second and third densities, respectively. The data points 402, 404, and 406 may then be associated with their respective density values by the calibration determination and correlation system 230, and stored in the memory 225, so that an appropriate zero calibration value may be chosen by the calibration selection system 240 during future measurements.

For example, similarly to the implementation of FIG. 3, it may be the case that (in this case, three) different fluids are alternately processed through the same flowmeter, where each of the three different fluids has a density corresponding to one of the data points 402, 404, and 406. In one implementation, then, the calibration selection system 240 might simply select a zero calibration value corresponding to a measured one of the three densities, perhaps from a table relating the zero calibration and density values and stored in the memory 235.

In another example, a fluid may be used having a density that does not directly correspond to one of the data points 402, 404, or 406. In this case, the three data points 402, 404, and 406 may nonetheless be used to obtain an appropriate zero calibration value. For example, a number of density bands 408, 410, 412, 414, 416, and 418 might be defined within a relevant density range, so that the zero calibration values corresponding to the data points 402, 404, and 406 may be associated with a corresponding one of the density bands. The bands may be established in the calibration determination and correlation system 230 and/or the calibration selection system 240, and stored in the memory 235. The bands may be based on, for example, a manufacturer's determination, or could be a configurable parameter that is adjusted by a user of the flowmeter.

Once the bands are established for a fluid having a density within one of the bands, an appropriate zero calibration value may be chosen. For example, if a fluid having a density falling within the density band 410 is processed by the flowmeter, then the zero calibration value corresponding to the data point 402 may be used.

Somewhat similarly, if the data points 402, 404, and 406 have some type of relationship to one another, such as a linear, quasi-linear, or tractable relationship, the calibration determination and correlation system 230 may interpolate (e.g., linearly interpolate) between the data points. In this way, a fluid having a density anywhere within the relevant range could be correlated with a corresponding zero calibration value that would produce an improved-accuracy measurement. In this case, the memory 235 may be used to store a mathematical relationship or algorithm derived by the calibration determination and correlation system 230, rather than (or in addition to) a table of related values.

Figure 5:
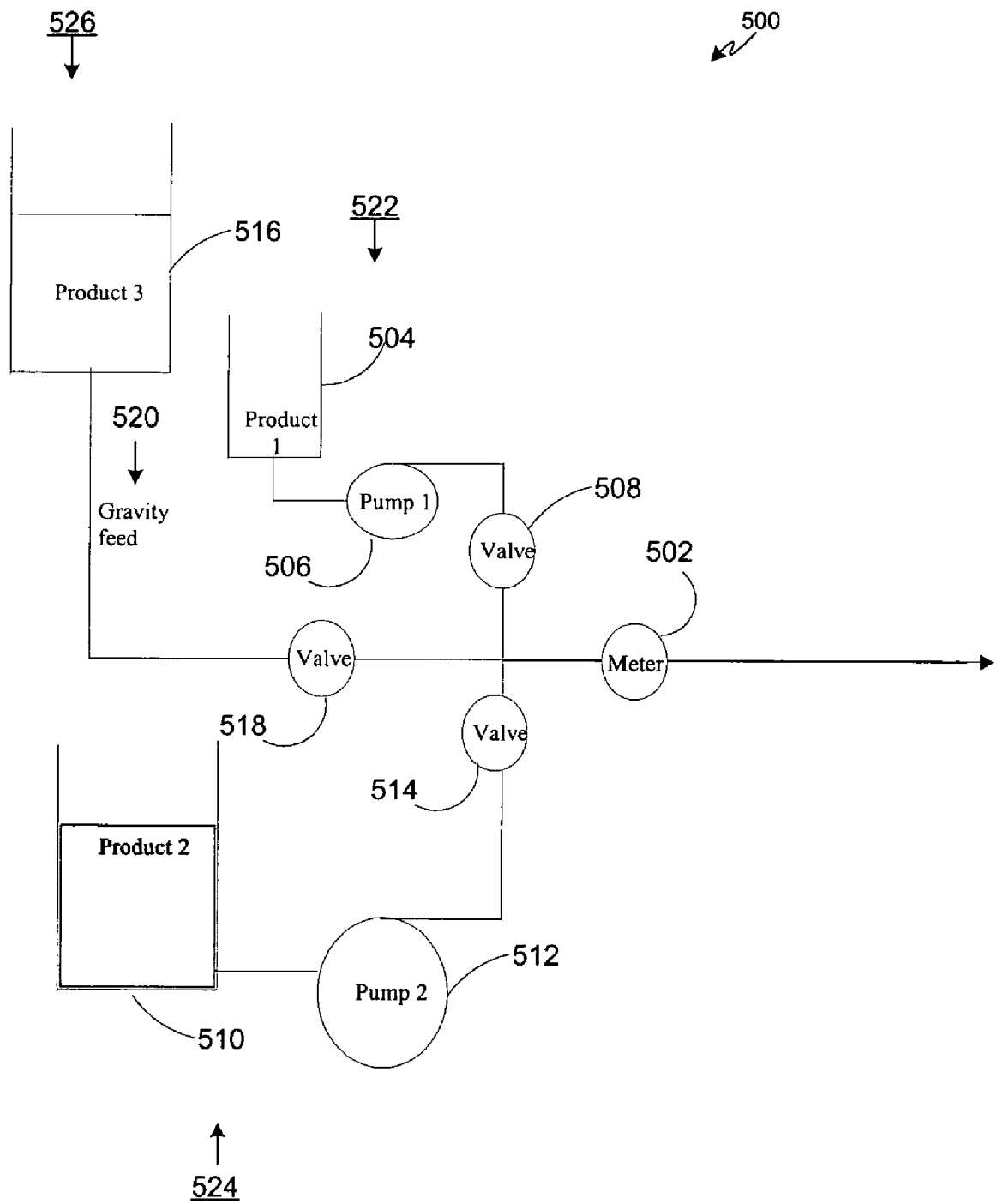
FIG. 5 is a block diagram of a flowmeter operating in conjunction with a plurality of piping and/or pumping configurations.

FIG. 5 is a block diagram 500 of a flowmeter 502 operating in conjunction with a plurality of piping and/or pumping configurations. In FIG. 5, a first material or product 504 is pumped through a pump 506 and a valve 508 before reaching the meter 502. A second product 510 is pumped through a pump 512 and a valve 514 before reaching the meter 502. Finally in FIG. 5, a third product 516 is sent to the meter 502 after being fed to a valve 518 by way of a gravity feed 520. Thus, the first product 504, the pump 506, and the valve 508 form a first configuration 522, the second product 510, the pump 512, and the valve 514 form a second configuration 524, and the third product 516, valve 518, and the gravity feed 520 form a third configuration 526.

In FIG. 5, the three products 504, 510, and 516 may or may not have the same density as one another. Even in the case where two or more of the densities are the same (or even where two of the products are the same), however, zero calibration values associated with each of the configurations 522, 524, and 526 may be different from one another, due to, for example, the configuration elements (e.g., the valves 508, 514, 518, the pumps 506 and 512, or the gravity feed 520) that are used, and/or the manner in which the configuration elements are connected to one another.

Thus, in one exemplary case, and similar to the chart of FIG. 4, a zero calibration value is determined for (and associated with) each of the configurations 522, 524, and 526, and stored for future use. Selection of an appropriate zero calibration value is then determined during measurements by way of discrete input from an operator of the flowmeter 502, e.g., by input into the calibration determination and correlation system 230 and/or the calibration selection system 240 of a currently-used configuration.

In a more specific example, the various zero calibration values are associated with their respective configurations in the above-described manner, and the configurations and corresponding zero calibration values are then displayed on an output screen associated with the digital transmitter 104. In this way, a user may simply scroll through the stored configurations to select an appropriate zero calibration value.

In a further example, if the three products have different densities, then these densities are correlated with a specific configuration and corresponding zero calibration value. Then, during measurements, the flowmeter determines a density of a currently-measured product, and thereby determines the appropriate zero calibration value automatically. In other words, the meter 502 determines that, based on a given density of a current product, a particular configuration exists. Then, based on that density and configuration, the appropriate zero calibration value may be selected.

Figure 6:
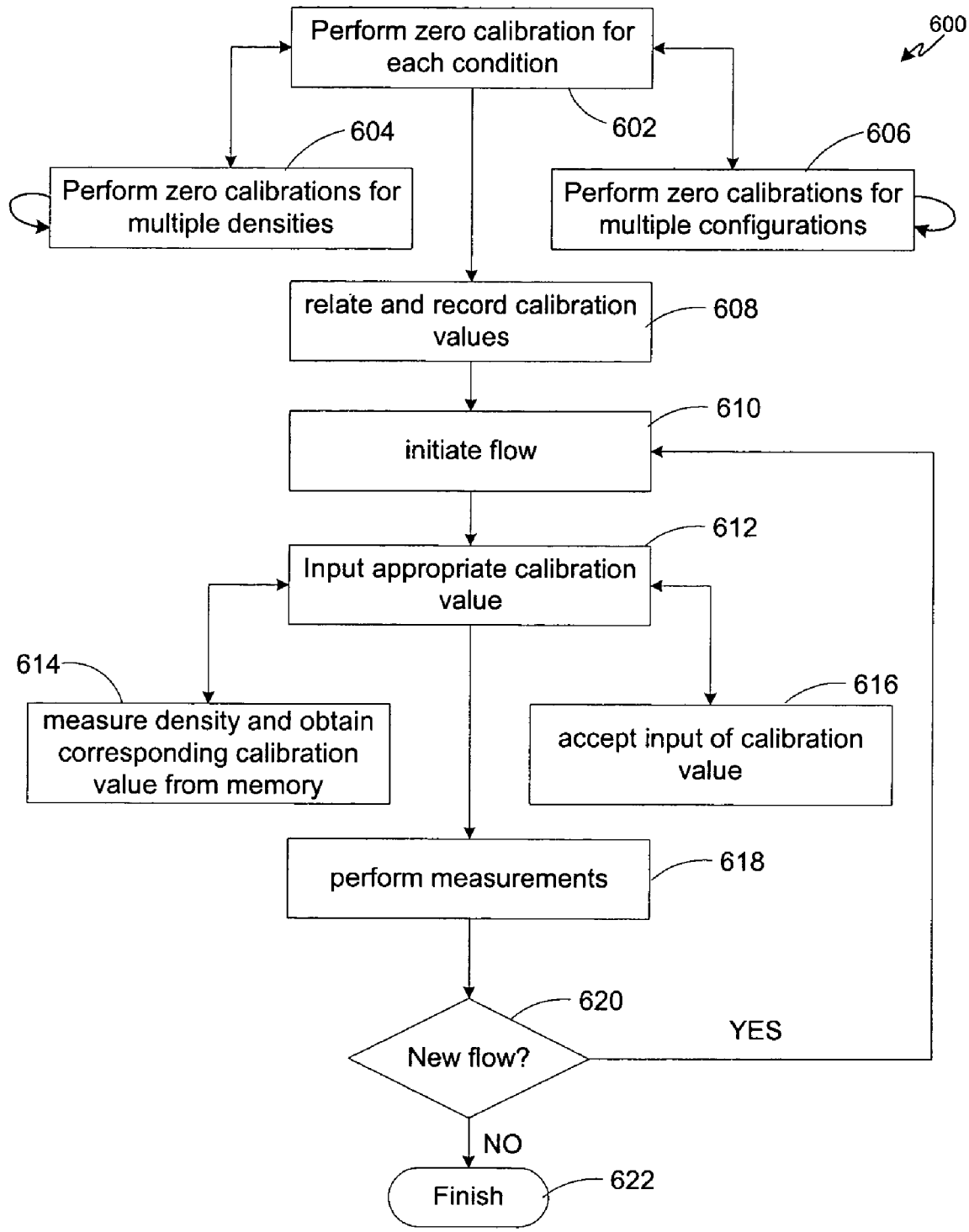
FIG. 6 is a flowchart illustrating techniques for selecting a zero calibration value.

FIG. 6 is a flowchart 600 illustrating techniques for selecting a zero calibration value, as described above. In FIG. 6, it is assumed that a particular flowtube or flowtube type is being used. Thus, if a new or different flowtube were used, the process(es) described below may require repeating to ensure accuracy of the flowmeter in conjunction with the new flowtube.

To begin, a user performs a zero calibration for each condition, i.e., for each operational parameter (602). As in the examples above, this might include performing zero calibrations for materials having multiple, different densities (604), or might include performing zero calibrations for multiple, different configurations (606), or both. The zero calibration values are related to their corresponding operational parameters by the calibration determination and correlation system 230, and these values and their relations to one another (including, possibly, a mathematical relationship between the values) are recorded in the memory 235 (608).

Then, flow of a particular material (in a particular configuration) is commenced (610). The appropriate zero calibration value is selected by the calibration selection system 240 (612). For example, the flowmeter may be used to measure a density of the currently-flowing fluid, whereupon the density is correlated with a particular zero calibration value in one or more of the manners described above (614). As another example, the zero calibration value may be selected based on a current configuration/product being used, as input by a user, perhaps by way of a scrolling, input/output display (616).

Measurements are then performed for some period of time (618). If characteristics of a new material(s) and/or configuration are to be measured (620), then flow of that material (in that configuration) is initiated (610), and the zero calibration value is adjusted accordingly. Otherwise, the process flow ends (622).

Although density and mechanical configurations are primarily discussed above as examples of operational parameters that may affect zero calibration value selection, other factors may affect selection of an appropriate zero calibration value. For example, a zero calibration value may be temperature dependent for wide swings in temperature of, for example, approximately 40 or 50 C or greater. The various procedures described above can be done with such variations in temperature, since temperature also is measured (specifically, using the temperature sensor 220).

The techniques described above can be performed, for example, by a manufacturer, during installation of the flowmeter. Alternatively, the techniques can be performed by a user of the flowmeter, periodically or during routine measurements. The techniques may be advantageous during cleaning of the flowmeter, during which cleaning materials may be processed through the flowmeter.

Many types of materials may be used in conjunction with the implementations described herein. For example, the flowmeter zeroing techniques may be used to measure a density and/or mass flow of liquids such as petroleum oil (e.g., Naphtha, natural or distilled) or other hydrocarbon materials, food and food-related materials, as well as cleaning materials. Similarly, the flowmeter and zeroing techniques may be used to measure density and/or mass flow of various gasses, including air, natural gas, and elemental gasses such as Helium. As a result, applications for these and related techniques are far-ranging, including food industries, drug production, oil and gas processing, and various other industries.

Moreover, although the implementations discussed above consider the direct integration of zeroing techniques with a flowmeter, such as implementing the techniques in a software module associated with the digital transmitter 104, it is also possible to determine zero calibration values independently of the particular transmitter or control system being used. In this case, the zero calibration values could be externally subtracted from (or added to) a measurement output of the digital transmitter 104.

A number of implementations have been described. Nevertheless, it will be understood that various modifications may be made. Accordingly, other implementations are within the scope of the following claims.

What is claimed is:

1. A method of operating a flowmeter comprising:
determining an operational parameter associated with the flowmeter, based on a sensor signal received from a sensor, the sensor being operable to measure vibrations of a vibratable flowtube associated with the flowmeter;
determining a zero-flow calibration value based on the operational parameter, and based on a plurality of previously-determined zero-flow calibration values;
taking a measurement of a property of a material within the flowtube associated with the flowmeter, using the flowmeter; and
adjusting the measurement using the zero-flow calibration value.

2. The method of claim 1 wherein determining the operational parameter includes determining a configuration of flow elements associated with the flowtube.

3. The method of claim 2 wherein determining the zero-flow calibration value comprises selecting the zero-flow calibration value from among the previously-determined zero-flow calibration values as being the zero-flow calibration value that corresponds to one of a set of configurations, where each of the set of configurations existed at a time when its corresponding zero-flow calibration value was previously determined.

4. The method of claim 2 wherein determining the operational parameter comprises accepting a selection of the configuration from a pre-determined set of configurations.

5. The method of claim 2 wherein determining the operational parameter comprises:
measuring a density of the material; and
associating the density with a first configuration.

6. The method of claim 1 wherein the operational parameter includes a density of the material in the flowtube.

7. The method of claim 6 wherein determining the zero-flow calibration value comprises:
associating the density with a range of densities; and
selecting the zero-flow calibration value from among the plurality of previously-determined zero-flow calibration values, based on a pre-determined relationship between the range of densities and the zero-flow calibration value.

8. The method of claim 6 wherein determining the zero-flow calibration value comprises inputting the density into a mathematical relationship derived from a relationship between the previously-determined zero-flow calibration values and corresponding density measurements.

9. The method of claim 1 wherein determining the zero-flow calibration value comprises selecting the zero-flow calibration value from among the plurality of previously-determined zero-flow calibration values, based on a pre-determined relationship between the operational parameter and the zero-flow calibration value.

10. The method of claim 1 wherein determining the operational parameter includes determining a gas void fraction of the material in the flowtube.

11. The method of claim 10 wherein determining the gas void fraction comprises receiving a current gas void fraction from a gas void fraction measurement system, and further wherein determining the zero-flow calibration value comprises selecting a current zero-flow calibration value previously associated with the current gas void fraction measurement.

12. A flowmeter comprising:
a vibratable flowtube;
at least one sensor coupled to the vibratable flowtube, the sensor being operable to measure vibrations of the vibratable flowtube;
a processing device coupled to the sensor, the processing device configured to:
determine an operational parameter associated with the flowmeter based on a sensor signal received from the sensor;
determine a zero-flow calibration value based on the operational parameter, and based on a plurality of previously-determined zero-flow calibration values;
take a measurement of a property of a material within the flowtube associated with the flowmeter, using the flowmeter; and adjust the measurement using the zero-flow calibration value.

13. The flowmeter of claim 12 wherein, to determine the operational parameter, the processing device is configured to determine a configuration of flow elements associated with the flowtube.

14. The flowmeter of claim 13 wherein, to determine the zero-flow calibration value, the processing device is configured to select the zero-flow calibration value from among the previously-determined zero-flow calibration values as being the zero-flow calibration value that corresponds to one of a set of configurations, where each of the set of configurations existed at a time when its corresponding zero-flow calibration value was previously determined.

15. The flowmeter of claim 13 wherein, to determine the operational parameter, the processing device is configured to accept a selection of the configuration from a pre-determined set of configurations.

16. The flowmeter of claim 13 wherein, to determine the operational parameter, the processing device is configured to:
measure a density of the material; and
associate the density with a first configuration.

17. The flowmeter of claim 12 wherein the operational parameter includes a density of the material in the flowtube.

18. The flowmeter of claim 17 wherein, to determine the zero-flow calibration value, the processing device is configured to:
associate the density with a range of densities; and
select the zero-flow calibration value from among the plurality of previously-determined zero-flow calibration values, based on a pre-determined relationship between the range of densities and the zero-flow calibration value.

19. The flowmeter of claim 17 wherein, to determine the zero-flow calibration value, the processing device is configured to input the density into a mathematical relationship derived from a relationship between the previously-determined zero-flow calibration values and corresponding density measurements.

20. The flowmeter of claim 12 wherein, to determine the zero-flow calibration value, the processing device is configured to select the zero-flow calibration value from among the plurality of previously-determined zero-flow calibration values, based on a pre-determined relationship between the operational parameter and the zero-flow calibration value.

21. The flowmeter of claim 12 wherein, to determine the operational parameter, the processing device is configured to determine a gas void fraction of the material in the flowtube.

22. The flowmeter of claim 21 wherein, to determine the gas void fraction, the processing device is configured to receive a current gas void fraction from a gas void fraction measurement system, and further wherein, to determine the zero-flow calibration value, the processing device is configured to select a current zero-flow calibration value previously associated with the current gas void fraction measurement.

23. A transmitter for use with a flowmeter that includes a vibratable flowtube and at least one sensor coupled to the vibratable flowtube, the sensor being operable to measure vibrations of the vibratable flowtube, the transmitter comprising:
a processing device coupled to the sensor, the processing device configured to:
determine an operational parameter associated with the flowmeter based on a sensor signal received from a sensor;
determine a zero-flow calibration value based on the operational parameter, and based on a plurality of previously-determined zero-flow calibration values;
take a measurement of a property of a material within the flowtube, using the flowmeter; and
adjust the measurement using the zero-flow calibration value.

24. The transmitter of claim 23 wherein, to determine the operational parameter, the processing device is configured to determine a configuration of flow elements associated with the flowtube.

25. The transmitter of claim 24 wherein, to determine the zero-flow calibration value, the processing device is configured to select the zero-flow calibration value from among the previously-determined zero-flow calibration values as being the zero-flow calibration value that corresponds to one of a set of configurations, where each of the set of configurations existed at a time when its corresponding zero-flow calibration value was previously determined.

26. The transmitter of claim 24 wherein, to determine the operational parameter, the processing device is configured to accept a selection of the configuration from a pre-determined set of configurations.

27. The transmitter of claim 24 wherein, to determine the operational parameter, the processing device is configured to:
measure a density of the material; and
associate the density with a first configuration.

28. The transmitter of claim 23 wherein the operational parameter includes a density of the material in the flowtube.

29. The transmitter of claim 28 wherein, to determine the zero-flow calibration value, the processing device is configured to:
associate the density with a range of densities; and
select the zero-flow calibration value from among the plurality of previously-determined zero-flow calibration values, based on a pre-determined relationship between the range of densities and the zero-flow calibration value.

30. The transmitter of claim 28 wherein, to determine the zero-flow calibration value, the processing device is configured to input the density into a mathematical relationship derived from a relationship between the previously-determined zero-flow calibration values and corresponding density measurements.

31. The transmitter of claim 23 wherein, to determine the zero-flow calibration value, the processing device is configured to select the zero-flow calibration value from among the plurality of previously-determined zero-flow calibration values, based on a pre-determined relationship between the operational parameter and the zero-flow calibration value.

32. The transmitter of claim 23 wherein, to determine the operational parameter, the processing device is configured to determine a gas void fraction of the material in the flowtube.

33. The transmitter of claim 32 wherein, to determine the gas void fraction, the processing device is configured to receive a current gas void fraction from a gas void fraction measurement system, and further wherein, to determine the zero-flow calibration value, the processing device is configured to select a current zero-flow calibration value previously associated with the current gas void fraction measurement.

* * * * *